(12) United States Patent
Nakai et al.

(10) Patent No.: US 12,109,335 B2
(45) Date of Patent: *Oct. 8, 2024

(54) COMPOSITION FOR ACOUSTIC WAVE PROBE, SILICONE RESIN FOR ACOUSTIC WAVE PROBE, ACOUSTIC WAVE PROBE, ULTRASOUND PROBE, ACOUSTIC WAVE MEASUREMENT APPARATUS, ULTRASOUND DIAGNOSTIC APPARATUS, PHOTOACOUSTIC WAVE MEASUREMENT APPARATUS, AND ULTRASOUND ENDOSCOPE

(71) Applicants: FUJIFILM Corporation, Tokyo (JP); Shin-Etsu Chemical Co., Ltd., Tokyo (JP)

(72) Inventors: Yoshihiro Nakai, Kanagawa (JP); Shigeki Uehira, Kanagawa (JP); Taichi Kitagawa, Annaka (JP); Nobuaki Matsumoto, Annaka (JP)

(73) Assignees: FUJIFILM Corporation, Tokyo (JP); Shin-Etsu Chemical Co., Ltd., Tokyo (JP)

( * ) Notice: Subject to any disclaimer, the term of this patent is extended or adjusted under 35 U.S.C. 154(b) by 869 days.

This patent is subject to a terminal disclaimer.

(21) Appl. No.: 16/811,636

(22) Filed: Mar. 6, 2020

(65) Prior Publication Data

US 2020/0206393 A1 Jul. 2, 2020

Related U.S. Application Data

(63) Continuation of application No. PCT/JP2018/033195, filed on Sep. 7, 2018.

(30) Foreign Application Priority Data

Sep. 11, 2017 (JP) ................................ 2017-174405

(51) Int. Cl.

| | |
|---|---|
| *A61K 9/16* | (2006.01) |
| *A61B 5/00* | (2006.01) |
| *A61B 8/00* | (2006.01) |
| *A61B 8/12* | (2006.01) |
| *A61L 31/02* | (2006.01) |
| *A61L 31/06* | (2006.01) |
| *A61L 31/12* | (2006.01) |
| *A61L 31/14* | (2006.01) |
| *C08G 77/00* | (2006.01) |
| *C08L 83/04* | (2006.01) |
| *G01S 15/89* | (2006.01) |
| *G10K 11/30* | (2006.01) |

(52) U.S. Cl.
CPC .......... *A61L 31/129* (2013.01); *A61B 5/0095* (2013.01); *A61B 8/12* (2013.01); *A61B 8/4444* (2013.01); *A61L 31/028* (2013.01); *A61L 31/06* (2013.01); *A61L 31/128* (2013.01); *A61L 31/14* (2013.01); *C08G 77/70* (2013.01); *C08L 83/04* (2013.01); *G01S 15/8906* (2013.01); *G10K 11/30* (2013.01); *C08L 2205/025* (2013.01); *C08L 2205/03* (2013.01)

(58) Field of Classification Search
CPC .. A61K 9/5153; A61K 9/0019; A61K 9/0053; A61K 31/203; A61K 31/365; A61J 3/07; A61P 25/28
See application file for complete search history.

(56) References Cited

U.S. PATENT DOCUMENTS

| | | | |
|---|---|---|---|
| 10,245,006 | B2 | 4/2019 | Nakai et al. |
| 10,729,405 | B2 * | 8/2020 | Nakai ................. A61B 8/4281 |
| 2017/0000455 | A1 | 1/2017 | Nakai |
| 2017/0283677 | A1 | 10/2017 | Iwata |
| 2018/0344287 | A1 | 12/2018 | Nakai et al. |

FOREIGN PATENT DOCUMENTS

| | | | | |
|---|---|---|---|---|
| CN | 101081169 | A | 12/2007 | |
| CN | 105385166 | A | 3/2016 | |
| EP | 1172801 | B1 * | 4/2009 | ............. G10K 11/30 |
| EP | 3199591 | A1 * | 8/2017 | ............... C08K 3/00 |
| JP | 2015189818 | A | 11/2015 | |
| JP | 2016108395 | A | 6/2016 | |
| WO | 2016/038836 | A1 | 3/2016 | |
| WO | 2017130890 | A1 | 8/2017 | |

OTHER PUBLICATIONS

International Search Report issued in PCT/JP2018/033195; mailed Nov. 6, 2018.

(Continued)

*Primary Examiner* — Micah Paul Young
(74) *Attorney, Agent, or Firm* — Studebaker & Brackett PC

(57) ABSTRACT

A composition for an acoustic wave probe, containing the following ingredients (A) to (D): (A) a linear polysiloxane having a vinyl group; (B) a linear polysiloxane having two or more Si—H groups in a molecular chain; (C) a polysiloxane resin; and (D) surface-treated silica particles having an average primary particle diameter more than 16 nm and less than 100 nm, as well as, a silicone resin for an acoustic wave probe, an acoustic wave probe, an ultrasound probe, an acoustic wave measurement apparatus, an ultrasound diagnostic apparatus, a photoacoustic wave measurement apparatus, and an ultrasound endoscope, using the composition for an acoustic wave probe.

19 Claims, 1 Drawing Sheet

(56) References Cited

OTHER PUBLICATIONS

International Preliminary Report On Patentability and Written Opinion issued in PCT/JP2018/033195; issued Mar. 17, 2020.
The extended European search report issued by the European Patent Office on Oct. 7, 2020, which corresponds to European Patent Application No. 18854989.3-1102 and is related to U.S. Appl. No. 16/811,636.
An Office Action mailed by China National Intellectual Property Administration on Sep. 30, 2020, which corresponds to Chinese Patent Application No. 201880053568.6 and is related to U.S. Appl. No. 16/811,636 with English language translation.

* cited by examiner

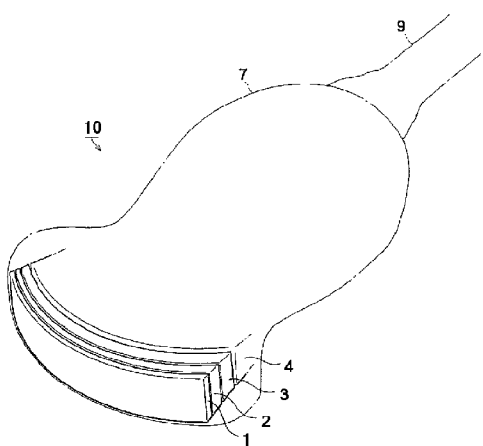

COMPOSITION FOR ACOUSTIC WAVE PROBE, SILICONE RESIN FOR ACOUSTIC WAVE PROBE, ACOUSTIC WAVE PROBE, ULTRASOUND PROBE, ACOUSTIC WAVE MEASUREMENT APPARATUS, ULTRASOUND DIAGNOSTIC APPARATUS, PHOTOACOUSTIC WAVE MEASUREMENT APPARATUS, AND ULTRASOUND ENDOSCOPE

CROSS-REFERENCE TO RELATED APPLICATIONS

This application is a Continuation of PCT International Application No. PCT/JP2018/033195 filed on Sep. 7, 2018, which claims priority under 35 U.S.C. § 119 (a) to Japanese Patent Application No. 2017-174405 filed in Japan on Sep. 11, 2017. Each of the above applications is hereby expressly incorporated by reference, in its entirety, into the present application.

TECHNICAL FIELD

The present invention relates to a composition for an acoustic wave probe, a silicone resin for an acoustic wave probe, an acoustic wave probe, an ultrasound probe, an acoustic wave measurement apparatus, an ultrasound diagnostic apparatus, a photoacoustic wave measurement apparatus, and an ultrasound endoscope.

BACKGROUND ART

In the acoustic wave measurement apparatus, an acoustic wave probe is used which irradiates a test object or a test site (hereinafter, simply referred to as an object) with an acoustic wave, receives a reflected wave (echo) thereof, and outputs a signal. An electrical signal converted from the reflected wave which has been received by this acoustic wave probe is displayed as an image. Accordingly, the interior of the test object is visualized and observed.

Ultrasonic waves, photoacoustic waves, or the like, which have an appropriate frequency in accordance with a test object, measurement conditions, or the like, are selected as the acoustic waves.

For example, the ultrasound diagnostic apparatus transmits an ultrasonic wave to the interior of a test object, receives the ultrasonic wave reflected by the tissues inside the test object, and displays the received ultrasonic wave as an image. The photoacoustic wave measurement apparatus receives an acoustic wave radiated from the interior of a test object due to a photoacoustic effect, and displays the received acoustic wave as an image. The photoacoustic effect is a phenomenon in which an acoustic wave (typically an ultrasonic wave) is generated through thermal expansion after a test object absorbs an electromagnetic wave and generates heat in a case where the test object is irradiated with an electromagnetic wave pulse of visible light, near infrared light, microwave, or the like.

Since the acoustic wave measurement apparatus performs transmission and reception of an acoustic wave on a living body which is a test object, it is required to fulfill requirement of consistency in the acoustic impedance within, for example, the living body (typically, the human body) and is required decrease in acoustic attenuation.

For example, a probe for an ultrasound diagnostic apparatus (also referred to as an ultrasound probe) which is a kind of acoustic wave probe includes a piezoelectric element which transmits and receives an ultrasonic wave and an acoustic lens which is a portion coming into contact with a living body. An ultrasonic wave generated from the piezoelectric element is incident on the living body after being transmitted through the acoustic lens. In a case where the difference between acoustic impedance (density×acoustic velocity) of the acoustic lens and acoustic impedance of the living body is large, the ultrasonic wave is reflected by the surface of the living body and the ultrasonic wave is not efficiently incident on the living body. As a result, it is difficult to obtain a favorable resolution. In addition, it is desirable that ultrasonic attenuation of the acoustic lens is low in order to transmit and receive the ultrasonic wave with high sensitivity.

For this reason, a silicone resin of which the acoustic impedance is close to the acoustic impedance (in the case of a human body, $1.4 \times 10^6$ to $1.7 \times 10^6$ $kg/m^2/sec$) of a living body and which has a low ultrasonic attenuation is used as a material of the acoustic lens.

Furthermore, regarding the usage of the acoustic wave measurement apparatus, since transmission and reception of an acoustic wave is performed such that the acoustic wave probe is rubbed against a living body, certain hardness and mechanical strength are required. Since silicone resins are usually soft and have poor mechanical strength, attempts have been made to increase the hardness and the mechanical strength by mixing inorganic fillers with silicone resins or by introducing a crosslinked structure.

For example, Patent Literature 1 describes a composition for an ultrasound probe obtainable by mixing an inorganic filler into a mixture of at least three kinds of polyorganosiloxanes including a particular branched polyorganosiloxane, and a silicone resin for an ultrasound probe formed by curing this composition. This silicone resin for an ultrasonic probe is considered to have low ultrasonic attenuation, high resin hardness, and high mechanical strength (tensile strength at break, tensile elongation at break, and tear strength).

When an inorganic filler is incorporated into a silicone resin, the specific gravity of the silicone resin is increased, acoustic impedance is increased, and the acoustic impedance of the silicone resin can be made close to that of a living body. From this point of view, it is desirable to incorporate the inorganic filler in an amount that is large to some extent into the silicone resin. However, when the mixing amount of the inorganic filler becomes large, the viscosity of the composition before curing increases, and handling upon molding or the like may become difficult. As a technology for coping with this problem, Patent Literature 2 describes a composition for an acoustic wave probe, the composition containing a polysiloxane mixture that contains a polysiloxane having a vinyl group, a polysiloxane having two or more Si—H groups in a molecular chain, and surface-treated silica particles having an average primary particle diameter of more than 16 nm and less than 100 nm.

CITATION LIST

Patent Literatures

Patent Literature 1: JP-A-2015-189818
Patent Literature 2: WO 2017/130890 A1

SUMMARY OF INVENTION

Technical Problem

An acoustic wave probe is repeatedly used over a long period of time. The inventors of the present invention changed the viewpoint from the conventional viewpoint, and repeatedly conducted an investigation on the improvement of mechanical properties of acoustic wave probes also from the viewpoint of repeated long-term use. As a result, the inventors found that since an acoustic lens in particular is a portion used by rubbing or sometimes pressing against a living body, the acoustic lens is easily worn away due to long-term use, and this wear deforms the lens shape and causes an acoustic wave image to be out of focus. That is, the inventors conceived an idea that in addition to the above-mentioned improvement of mechanical properties such as tear strength, when abrasion resistance can be further enhanced, a significant contribution can be made to the improvement of performance or product quality of an acoustic wave probe.

The present invention is contemplated for providing a composition for an acoustic wave probe capable of realizing a silicone resin for an acoustic wave probe, the silicone resin having a predetermined viscosity, having an acoustic impedance close to the acoustic impedance of a living body, also having the acoustic attenuation suppressed, and having excellent tear strength as well as excellent abrasion resistance; and a silicone resin for an acoustic wave probe formed by curing this composition.

Furthermore, the present invention is contemplated for providing an acoustic wave probe, an ultrasound probe, an acoustic wave measurement apparatus, an ultrasound diagnostic apparatus, a photoacoustic wave measurement apparatus, and an ultrasound endoscope, all of these having a constituent member that is produced using the composition for an acoustic wave probe of the present invention.

Solution to Problem

The inventors of the present invention conducted a thorough investigation in view of the problems described above, and as a result, the inventors found that when a polysiloxane resin is further used in addition to a linear polysiloxane having a vinyl group and a linear polysiloxane having two or more Si—H groups in a molecular chain as raw materials of a silicone resin, the molecular structure of a silicone resin to be obtained is produced into a three-dimensional network structure into which a highly crosslinked structure different from the structure of conventional silicone resins has been introduced, and that when surface-treated silica particles having the average primary particle diameter in a particular range are incorporated, a silicone resin having sufficiently improved abrasion resistance can be obtained without impairing the high acoustic wave characteristics and mechanical strength according to the prior art technologies. The present invention was finally completed based on these findings.

The above problem has been solved by the following means.

<1>
A composition for an acoustic wave probe, comprising the following ingredients (A) to (D):
(A) a linear polysiloxane having a vinyl group;
(B) a linear polysiloxane having two or more Si—H groups in a molecular chain;
(C) a polysiloxane resin; and
(D) surface-treated silica particles having an average primary particle diameter more than 16 nm and less than 100 nm.
<2>
The composition for an acoustic wave probe described in the item <1>, wherein, in 100 parts by mass of a total of each content of the ingredients (A) to (D), the content of the ingredient (D) is 25 to 70 parts by mass.
<3>
The composition for an acoustic wave probe described in the item <1> or <2>,
wherein, in 100 parts by mass in the total of each content of the ingredients (A) to (D), the content of the ingredient (A) is 20 to 80 parts by mass, the content of the ingredient (B) is 0.1 to 20 parts by mass, and the content of the ingredient (C) is 0.1 to 50 parts by mass.
<4>
The composition for an acoustic wave probe described in any one of the items <1> to <3>,
wherein the ingredient (D) are silica particles subjected to surface treatment using a silane compound.
<5>
The composition for an acoustic wave probe described in the item <4>,
wherein the ingredient (D) are silica particles subjected to surface treatment using a trimethylsilylating agent.
<6>
The composition for an acoustic wave probe described in any one of the items <1> to <5>,
wherein a methanol hydrophobicity of the ingredient (D) is 40 to 80 mass %.
<7>
The composition for an acoustic wave probe described in any one of the items <1> to <6>,
wherein the ingredient (D) has a truly spherical shape.
<8>
The composition for an acoustic wave probe described in any one of the items <1> to <7>,
wherein the ingredient (A) has a phenyl group.
<9>
The composition for an acoustic wave probe described in any one of the items <1> to <8>,
wherein a mass average molecular weight of the ingredient (A) is 20,000 to 200,000.
<10>
The composition for an acoustic wave probe described in the item <9>,
wherein the mass average molecular weight is 40,000 to 150,000.
<11>
The composition for an acoustic wave probe described in any one of the items <1> to <10>,
wherein the ingredient (C) is a polysiloxane resin contains a $R_3SiO_{1/2}$ unit and a $SiO_{4/2}$ unit and has at least two vinyl groups in one molecule,
wherein a molar ratio of the $R_3SiO_{1/2}$ unit to the $SiO_{4/2}$ unit is 0.6 to 1.2, and
wherein R represents a monovalent hydrocarbon group.
<12>
The composition for an acoustic wave probe described in the item <11>,
wherein the ingredient (C) is constituted by the $R_3SiO_{1/2}$ unit and the $SiO_{4/2}$ unit.
<13>
The composition for an acoustic wave probe described in any one of the items <1> to <12>, comprising:
0.00001 to 0.01 parts by mass of platinum or a platinum compound with respect to 100 parts by mass of the total of each content of the ingredients (A) to (D).
<14>
A silicone resin for an acoustic wave probe which is obtained by curing the composition for an acoustic wave probe described in any one of the items <1> to <13>.

<15>

An acoustic wave probe, comprising at least one of an acoustic lens containing the silicone resin for an acoustic wave probe described in the item <14> and an acoustic matching layer containing the silicone resin for an acoustic wave probe described in the item <14> (an acoustic lens containing the silicone resin for an acoustic wave probe described in the item <14> and/or an acoustic matching layer containing the silicone resin for an acoustic wave probe described in the item <14>).

<16>

An ultrasound probe, comprising:
a capacitive micromachined ultrasonic transducer as an ultrasonic transducer array; and
an acoustic lens containing the silicone resin for an acoustic wave probe described in the item <14>.

<17>

An acoustic wave measurement apparatus, comprising:
the acoustic wave probe described in the item <15>.

<18>

An ultrasound diagnostic apparatus, comprising:
the acoustic wave probe described in the item <15>.

<19>

A photoacoustic wave measurement apparatus, comprising:
an acoustic lens containing the silicone resin for an acoustic wave probe described in the item <14>.

<20>

An ultrasound endoscope, comprising:
an acoustic lens containing the silicone resin for an acoustic wave probe described in the item <14>.

Unless otherwise specified in the description of the present specification, in a case where there are groups having a plurality of the same reference numerals as each other in general formulae representing compounds, these group may be the same as or different from each other, and a group (for example, an alkyl group) specified by each group may further have a substituent. In addition, the "Si—H group" means a group having three bonds on a silicon atom, but the description of the bonds is not repeated and the notation is simplified.

In addition, in the present specification, "to" means a range including numerical values denoted before and after "to" as a lower limit value and an upper limit value.

Unless otherwise specified, the mass average molecular weight in the present specification refers to a value (in terms of polystyrene) measured through gel permeation chromatography (GPC).

Effects of Invention

The composition for an acoustic wave probe of the present invention has a predetermined viscosity, and when the composition is cured, a silicone resin for an acoustic wave probe can be realized, the silicone resin having an acoustic impedance close to the acoustic impedance of a living body, having the acoustic attenuation suppressed, and having excellent tear strength as well as excellent abrasion resistance.

Furthermore, the silicone resin for an acoustic wave probe of the present invention has an acoustic impedance close to the acoustic impedance of a living body, has the acoustic attenuation suppressed, and also has excellent tear strength as well as excellent abrasion resistance.

Furthermore, the acoustic wave probe, ultrasound probe, acoustic wave measurement apparatus, ultrasound diagnostic apparatus, photoacoustic wave measurement apparatus, and ultrasound endoscope of the present invention each have a constituent member that is produced using the above-described composition for an acoustic wave probe having excellent performance.

BRIEF DESCRIPTION OF THE DRAWINGS

The FIGURE is a perspective transparent view of an example of a convex ultrasound probe which is an embodiment of an acoustic wave probe.

MODE FOR CARRYING OUT THE INVENTION

<<Composition for Acoustic Wave Probe>>

A composition for an acoustic wave probe (hereinafter, also simply referred to as a composition) of the present invention contains the following ingredients (A) to (D):
(A) a linear polysiloxane having a vinyl group (ingredient (A));
(B) a linear polysiloxane having two or more Si—H groups in a molecular chain (ingredient (B));
(C) a polysiloxane resin (ingredient (C)); and
(D) surface-treated silica particles having an average primary particle diameter more than 16 nm and less than 100 nm (ingredient (D)).

In 100 parts by mass of the total of each content of the ingredients (A) to (D), the content of the ingredient (D) is preferably 25 to 70 parts by mass, more preferably 30 to 60 parts by mass, and even more preferably 35 to 50 parts by mass. When the content of the silica particles is within the above-described range, the tear strength and the acoustic wave sensitivity are enhanced.

Furthermore, it is preferable that the contents of the ingredients (A) to (C) in 100 parts by mass of the total of each content of the ingredients (A) to (D) are in the following ranges.

The content of the ingredient (A) is preferably 20 to 80 parts by mass, more preferably 25 to 65 parts by mass, and further preferably 30 to 55 parts by mass. The content of the ingredient (B) is preferably 0.1 to 20 parts by mass, and more preferably 0.2 to 10 parts by mass. The content of the ingredient (C) is preferably 0.1 to 50 parts by mass, more preferably 5 to 20 parts by mass, and further preferably 8 to 18 parts by mass.

When the contents of the polysiloxanes and the polysiloxane resin are within the above-described ranges, the balance between the viscosity of the composition before curing, and the tear strength, abrasion resistance, and acoustic impedance of a cured product (silicone resin) to be obtained is excellent.

As described above, the composition of the present invention contains (A) a linear polysiloxane having a vinyl group (polyorganosiloxane) and (B) a linear polysiloxane having two or more Si—H groups in a molecular chain. However, it is preferable that the (B) linear polysiloxane having two or more Si—H groups in a molecular chain is (B) a linear polyorganosiloxane having two or more Si—H groups in a molecular chain.

Therefore, it is preferable that the composition of the present invention contains at least ingredient (A), (B) a linear polyorganosiloxane having two or more Si—H groups in a molecular chain (ingredient (B)), ingredient (C), and ingredient (D).

In the detailed description given below, a preferable embodiment including the ingredient (A), and (B) a linear polyorganosiloxane having two or more Si—H groups in a molecular chain (ingredient (B)) will be described. However, the present invention is not intended to be limited to the embodiment described below.

<(A) Linear Polysiloxane Having a Vinyl Group>

The ingredient (A) used in the present invention preferably has two or more vinyl groups in a molecular chain.

Examples of the ingredient (A) include polysiloxane (a1) having vinyl groups at least at both terminals of a molecular chain (hereinafter, simply referred to as ingredient (a1)), or polysiloxane (a2) having at least two —O—Si(CH$_3$)$_2$(CH=CH$_2$) in a molecular chain excluding terminal (hereinafter, simply referred to as polysiloxane (a2)). Among them, the polysiloxane (a1) having vinyl groups at least at both terminals of a molecular chain is preferable.

The polysiloxane (a2) is preferably polysiloxane (a2) in which —O—Si(CH$_3$)$_2$(CH=CH$_2$) is bonded to a Si atom constituting a main chain.

The ingredient (A) is subjected to hydrosilylation through a reaction with the ingredient (B), for example, in the presence of a platinum catalyst. A cross-linked structure (cured body) is formed through this hydrosilylation reaction (addition reaction).

The content of the vinyl group of the ingredient (A) is not particularly limited. The content of the vinyl group is, for example, preferably 0.01 to 5 mol % and more preferably 0.05 to 2 mol % from the viewpoint of forming a sufficient network between components contained in a composition for an acoustic wave probe.

Here, the content of the vinyl group is represented by mol % of the vinyl group-containing siloxane unit based on 100 mol % of all the units constituting the ingredient (A). One vinyl group-containing siloxane unit has 1 to 3 vinyl groups. Among them, one vinyl group is preferable for one vinyl group-containing siloxane unit. For example, in a case where all Si atoms of Si in a Si—O unit which constitutes a main chain and Si at a terminal have at least one vinyl group, the content becomes 100 mol %.

In addition, the ingredient (A) preferably has a phenyl group, and the content of the phenyl group of the ingredient (A) is not particularly limited. The content of the phenyl group is, for example, preferably 1 to 80 mol % and more preferably 2 to 40 mol % from the viewpoint of mechanical strength in a case where a silicone resin for an acoustic wave probe is made.

Here, the content of the phenyl group is represented by mol % of the phenyl group-containing siloxane unit based on 100 mol % of all the units constituting the polyorganosiloxane (A). One phenyl group-containing siloxane unit has 1 to 3 phenyl groups. Among them, two phenyl groups are preferable for one phenyl group-containing siloxane unit. For example, in a case where all Si atoms of Si in a Si—O unit which constitutes a main chain and Si at a terminal have at least one phenyl group, the content becomes 100 mol %.

The "unit" of polysiloxane refers to Si atoms in a Si—O unit which constitutes a main chain and at a terminal.

The degree of polymerization and the specific gravity are not particularly limited. The degree of polymerization is preferably 200 to 3,000 and more preferably 400 to 2,000, and the specific gravity is preferably 0.9 to 1.1 from the viewpoint of improving the mechanical strength (tear strength) and the chemical stability of an obtained silicone resin for an acoustic wave probe (hereinafter, also simply referred to as a "silicone resin"), as well as the viscosity of the composition before curing and the like.

The mass average molecular weight of the ingredient (A) is preferably 20,000 to 200,000, more preferably 40,000 to 150,000, and still more preferably 45,000 to 120,000 from the viewpoints of the mechanical strength of the silicone resin and the viscosity of the composition before curing.

The mass average molecular weight can be measured using, for example, TOLUENE (manufactured by Shonan Wako Junyaku K.K.) as an eluent, TSKgel G3000HXL+TSKgel G2000HXL (trade names) as columns, and a RI detector under the conditions of a temperature of 23° C. and a flow rate of 1 mL/min after preparing a GPC apparatus HLC-8220 (trade name, manufactured by TOSOH CORPORATION).

The kinematic viscosity of the ingredient (A) at 25° C. is preferably 1×10$^{-5}$ to 10 m$^2$/s, more preferably 1×10$^{-4}$ to 1 m$^2$/s, and still more preferably 1×10$^{-3}$ to 0.5 m$^2$/s.

The kinematic viscosity can be measured and obtained at a temperature of 25° C. using a Ubbelohde-type viscometer (for example, a trade name of SU manufactured by SIBATA SCIENTIFIC TECHNOLOGY LTD.) in compliance with JIS Z8803.

Polyorganosiloxane represented by General Formula (A) is preferable as the polyorganosiloxane (a1) having vinyl groups at least at both terminals of a molecular chain.

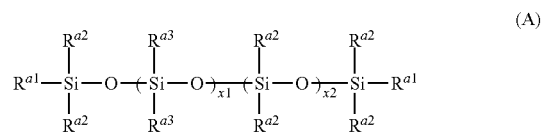

(A)

In General Formula (A), $R^{a1}$ represents a vinyl group and $R^{a2}$ and $R^{a3}$ each independently represent an alkyl group, a cycloalkyl group, an alkenyl group, or an aryl group. x1 and x2 each independently represent an integer of 1 or more.

The number of carbon atoms in an alkyl group in $R^{a2}$ and $R^{a3}$ is preferably 1 to 10, more preferably 1 to 4, still more preferably 1 or 2, and particularly preferably 1. Examples of the alkyl group include a methyl group, an ethyl group, an n-propyl group, an isopropyl group, an n-butyl group, an isobutyl group, an n-hexyl group, an n-octyl group, a 2-ethylhexyl group, and an n-decyl group.

The number of carbon atoms in a cycloalkyl group in $R^{a2}$ and $R^{a3}$ is preferably 3 to 10, more preferably 5 to 10, and still more preferably 5 or 6. In addition, the cycloalkyl group is preferably a 3-membered ring, a 5-membered ring, or a 6-membered ring, and more preferably a 5-membered ring or a 6-membered ring. Examples of the cycloalkyl group include a cyclopropyl group, a cyclopentyl group, and a cyclohexyl group.

The number of carbon atoms in an alkenyl group in $R^{a2}$ and $R^{a3}$ is preferably 2 to 10, more preferably 2 to 4, and still more preferably 2. Examples of the alkenyl group include a vinyl group, an allyl group, and a butenyl group.

The number of carbon atoms in an aryl group in $R^{a2}$ and $R^{a3}$ is preferably 6 to 12, more preferably 6 to 10, and still more preferably 6 to 8. Examples of the aryl group include a phenyl group, a tolyl group, and a naphthyl group.

The alkyl group, the cycloalkyl group, the alkenyl group, and the aryl group may have a substituent. Examples of such a substituent include a halogen atom, an alkyl group, a cycloalkyl group, an alkenyl group, an aryl group, an alkoxy group, an aryloxy group, an alkylthio group, an arylthio group, a silyl group, and a cyano group.

Examples of the group having a substituent include a halogenated alkyl group.

$R^{a2}$ and $R^{a3}$ are preferably an alkyl group, an alkenyl group, or an aryl group, more preferably an alkyl group having 1 to 4 carbon atoms, a vinyl group, or a phenyl group, and still more preferably a methyl group, a vinyl group, or a phenyl group.

Among them, $R^{a2}$ is preferably a methyl group. $R^{a3}$ is preferably a methyl group, a vinyl group, or a phenyl group, more preferably a methyl group or a phenyl group, and particularly preferably a phenyl group.

x1 is preferably an integer of 200 to 3,000 and more preferably an integer of 400 to 2,000.

x2 is preferably an integer of 1 to 3,000, more preferably an integer of 1 to 1,000, still more preferably an integer of 40 to 1,000, and particularly preferably an integer of 40 to 700.

In addition, as another embodiment, x1 is preferably an integer of 1 to 3,000 and more preferably an integer of 5 to 1,000.

In the present invention, each of repeating units "—Si $(R^{a3})_2$—O—" and "—Si$(R^{a2})_2$—O—" in General Formula (A) may exist in a block polymerized form, or may be in a form existing randomly.

Examples of the polyorganosiloxane having vinyl groups at least at both terminals of a molecular chain include DMS series (for example, DMS-V31, DMS-V31S15, DMS-V33, DMS-V35, DMS-V35R, DMS-V41, DMS-V42, DMS-V46, DMS-V51, and DMS-V52), and PDV series (for example, PDV-0341, PDV-0346, PDV-0535, PDV-0541, PDV-1631, PDV-1635, PDV-1641, and PDV-2335), PMV-9925, PVV-3522, FMV-4031, and EDV-2022 all of which are trade names manufactured by GELEST, INC.

In the DMS-V31S15, fumed silica is formulated into DMS-V31S15 in advance, and therefore, kneading using a special device is unnecessary.

The ingredient (A) in the present invention may be used singly or in a combination of two or more thereof.

<(B) Linear Polysiloxan Having Two or More Si—H Groups in Molecular Chain>

The ingredient (B) used in the present invention has two or more Si—H groups in a molecular chain. In a case where the ingredient (B) has a "—SiH$_2$—" structure, the number of the Si—H groups in the "—SiH$_2$—" structure is 2. In addition, in a case where the ingredient (B) has a "—SiH$_3$—" structure, the number of the Si—H groups in the "—SiH$_3$—" structure is 3.

The ingredient (B) having two or more Si—H groups in a molecular chain, it is possible to crosslink polyorganosiloxane having at least two polymerizable unsaturated groups.

The mass average molecular weight of the ingredient (B) is preferably 500 to 100,000 and more preferably 1,500 to 50,000 from the viewpoints of the mechanical strength of the silicone resin and the viscosity of the composition before curing.

The ingredient (B) is preferably polyorganosiloxane represented by General Formula (B).

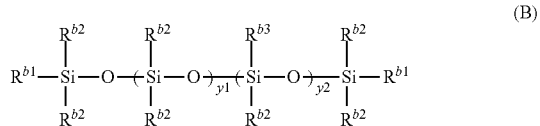

(B)

In General Formula (B), $R^{b1}$ to $R^{b3}$ each independently represent a hydrogen atom, an alkyl group, a cycloalkyl group, an alkenyl group, or an aryl group. y1 and y2 each independently represent an integer of 1 or more. However, there are two or more Si—H groups in a molecular chain.

An alkyl group, a cycloalkyl group, an alkenyl group, and an aryl group in $R^{b1}$ to $R^{b3}$ are synonymous with an alkyl group, a cycloalkyl group, an alkenyl group, and an aryl group in $R^{a2}$ and $R^{a3}$, and preferred ranges thereof are also the same as each other.

$R^{b1}$ to $R^{b3}$ are preferably a hydrogen atom, an alkyl group, an alkenyl group, or an aryl group, and more preferably a hydrogen atom, an alkyl group having 1 to 4 carbon atoms, a vinyl group, or a phenyl group.

Among them, $R^{b1}$ and $R^{b2}$ are preferably a hydrogen atom, an alkyl group, an alkenyl group, or an aryl group, more preferably a hydrogen atom or an alkyl group, still more preferably a hydrogen atom or a methyl group, and particularly preferably a methyl group.

$R^{b3}$ is preferably a hydrogen atom, an alkyl group, an alkenyl group, or an aryl group, more preferably a hydrogen atom or an aryl group, still more preferably a hydrogen atom or a phenyl group, and particularly preferably a hydrogen atom.

y1 is preferably an integer of 0 to 2,000, more preferably an integer of 0 to 1,000, and still more preferably an integer of 0 to 30.

y2 is preferably an integer of 1 to 2,000, more preferably an integer of 1 to 1,000, and still more preferably an integer of 1 to 30.

y1+y2 is preferably an integer of 5 to 2,000, more preferably an integer of 7 to 1,000, still more preferably an integer of 10 to 50, and particularly preferably an integer of 15 to 30.

In the present invention, each of repeating units "—Si$(R^{b2})_2$—O—" and "—Si$(R^{b2})(R^{b3})_2$—O—" in General Formula (B) may exist in a block polymerized form or may be in a form existing randomly in polysiloxane.

As a combination of $R^{b1}$ to $R^{b3}$, a combination of a hydrogen atom or an alkyl group having 1 to 4 carbon atoms as $R^{b1}$, an alkyl group having 1 to 4 carbon atoms as $R^{b2}$, and a hydrogen atom as $R^{b3}$ is preferable and a combination of an alkyl group having 1 to 4 carbon atoms as $R^{b1}$, an alkyl group having 1 to 4 carbon atoms as $R^{b2}$, and a hydrogen atom as $R^{b3}$ is more preferable.

In the preferred combinations, the content of a hydrosilyl group represented by y2/(y1+y2) is preferably greater than 0.1 and less than or equal to 1.0 and more preferably greater than 0.2 and less than or equal to 1.0.

Examples of the ingredient (B) include HMS-064 (MeHSiO: 5 to 7 mol %), HMS-082 (MeHSiO: 7 to 8 mol %), HMS-301 (MeHSiO: 25 to 30 mol %), and HMS-501 (MeHSiO: 50 to 55 mol %) as methylhydrosiloxane-dimethylsiloxane copolymers (trimethylsiloxane terminated), HPM-502 (MeHSiO: 45 to 50 mol %) as a methylhydrosiloxane-phenylmethylsiloxane copolymer, and HMS-991 (MeHSiO: 100 mol %) as a methylhydrosiloxane polymer, all of which are trade names of GELEST, INC.

Here, the mol % of MeHSiO has the same meaning as a value obtained by multiplying y2/(y1+y2) in the above-described preferred combination of $R^{b1}$ to $R^{b3}$ by 100.

It is preferable that the ingredient (B) has no vinyl group from the viewpoint of preventing the progress of a crosslinking reaction within a molecule.

The ingredient (B) used in the present invention may be used singly, or in a combination of two or more thereof.

<(C) Polysiloxane Resin>

The polysiloxane resin is a polysiloxane compound having a three-dimensional network structure. The ingredient (C) used in the present invention is not particularly limited;

however, a polysiloxane resin containing a $SiO_{4/2}$ unit (unit Q) and a $R_3SiO_{1/2}$ unit (unit M) is preferred. In the unit M, R represents a monovalent hydrocarbon group. R may or may not have a carbon-carbon unsaturated bond. It is preferable that at least one of the units M that constitute the polysiloxane resin contains a monovalent unsaturated hydrocarbon group having a carbon-carbon unsaturated bond. However, this carbon-carbon unsaturated bond does not include a carbon-carbon double bond of an aromatic ring.

The number of carbon atoms of the above-described monovalent hydrocarbon group having no carbon-carbon unsaturated bond is preferably 1 to 18, more preferably 1 to 10, and particularly preferably 1 to 8. Specific examples include alkyl groups such as methyl, ethyl, propyl, i-propyl, butyl, isobutyl, t-butyl, pentyl, neopentyl, hexyl, cyclohexyl, octyl, nonyl, and decyl; aryl groups such as phenyl, tolyl, xylyl, and naphthyl; aralkyl groups such as benzyl, phenylethyl, and phenylpropyl; and monovalent groups obtained by substituting a portion or all of the hydrogen atoms of these groups with at least one of a halogen atom such as a fluorine atom, a bromine atom, or a chlorine atom, a cyano group, and the like, for example, chloromethyl, chloropropyl, bromoethyl, trifluoropropyl, and cyanoethyl. Among these, methyl is preferred.

The number of carbon atoms of the above-described monovalent unsaturated hydrocarbon group having a carbon-carbon unsaturated bond is preferably 2 to 18, more preferably 2 to 10, further preferably 2 to 8, and particularly preferably 2 to 6. Examples of the monovalent unsaturated hydrocarbon group having a carbon-carbon unsaturated bond include an alkenyl group and an alkynyl group and an alkenyl group is preferable. Examples of the monovalent unsaturated hydrocarbon group having a carbon-carbon unsaturated bond include vinyl, allyl, propenyl, i-propenyl, butenyl, hexenyl, cyclohexenyl and octenyl. Among these, vinyl is preferable.

The molar ratio (M/Q) of the $R_3SiO_{1/2}$ unit (unit M) to the $SiO_{4/2}$ unit (unit Q) is preferably 0.1 to 3.0, more preferably 0.3 to 2.5, even more preferably 0.5 to 2.0, and particularly preferably 0.6 to 1.2. When the molar ratio between the unit M and the unit Q is within the above-described range, the abrasion resistance and acoustic wave sensitivity of the silicone resin can be further enhanced. Meanwhile, the ingredient (C) may contain an $R_2SiO_{2/2}$ unit (unit D) and an $RSiO_{3/2}$ unit (unit T) in the molecule. R in the unit D and the unit T has the same meaning as R in the unit M, and the preferred range is also the same.

The ingredient (C) preferably contains at least two monovalent unsaturated hydrocarbon groups having a carbon-carbon unsaturated bond in one molecule. The content of the monovalent unsaturated hydrocarbon group having a carbon-carbon unsaturated bond in the ingredient (C) is more preferably $1 \times 10^{-5}$ to $1 \times 10^{-2}$ mol/g, and particularly preferably $1 \times 10^{-4}$ to $2 \times 10^{-3}$ mol/g.

In regard to the composition of the present invention, a resin matrix is formed by means of the ingredient (C), and an entirely uniform cured product is formed. Since the mechanical strength of this cured product is excellent, it is preferable that the ingredient (C) is formed from a $SiO_{4/2}$ unit (unit Q) and an $R_3SiO_{1/2}$ unit (unit M) and has at least two vinyl groups in one molecule.

It is more preferable that the ingredient (C) is formed from one kind of unit Q ($SiO_{4/2}$ unit) and two kinds of units M ($R^1_2R^2SiO_{1/2}$ unit and $R^1_3SiO_{1/2}$ unit).

Here, $R^1$ represents the above-described monovalent hydrocarbon group having no carbon-carbon unsaturated bond, and $R^2$ represents the above-described unsaturated hydrocarbon group.

The ingredient (C) is particularly preferably represented by the following average composition formula (1).
Average Composition Formula (1):

$$(SiO_{4/2})_b(R^1_2R^2SiO_{1/2})_c(R^1_3SiO_{1/2})_d$$

In the formula, b, c, and d each represent an integer; $R^1$ represents the above-described monovalent hydrocarbon group having no carbon-carbon unsaturated bond; and $R^2$ represents the above-described unsaturated hydrocarbon group.

In the present invention, the ingredient (C) is a solid or a viscous liquid at room temperature (25° C.). The mass average molecular weight of the ingredient (C) is not particularly limited; however, the mass average molecular weight is preferably a mass average molecular weight that gives a dynamic viscosity of a 50 mass % xylene solution of the ingredient (C) of 0.5 to 10 mm²/s, and more preferably 1.0 to 5.0 mm²/s. The dynamic viscosity is a value measured at 25° C. using an Ubbelohde type Ostwald viscometer. When the viscosity of the ingredient (C) is within the above-described range, it is preferable because the physical characteristics of the composition are not deteriorated.

Polysiloxane resins can be obtained from the market. For example, VQX-221 (xylene solution) commercially available from Gelest, INC can be used.

The ingredient (C) used in the present invention may be used singly, or in a combination of two or more thereof.

<(D) Surface-Treated Silica Particles Having an Average Primary Particle Diameter More than 16 nm and Less than 100 nm>

The ingredient (D) used in the present invention are silica particles of which an average primary particle diameter exceeds 16 nm and less than 100 nm and which have been subjected to surface treatment.

An effect of improving the acoustic impedance, the hardness, and the mechanical strength of a silicone resin is obtained by adding silica particles to the silicone resin. However, the acoustic attenuation increases with an increase in the amount of the silica particles added, and in a case where the addition amount is too large, the viscosity of the composition for an acoustic wave probe before curing increases.

However, in regard to the composition of the present invention, it is speculated that when a surface-treated ingredient (D) having an average primary particle diameter in a particular range is used, it is possible to decrease the viscosity of the composition before curing and to reduce the acoustic attenuation of the silicone resin. The reason for this is still not clearly understood; however, the reason is speculated as follows.

That is, in a case where silica particles having a small average primary particle diameter are used, the tear strength of the silicone resin is improved and increase in the acoustic attenuation is suppressed, whereas the viscosity of the composition for an acoustic wave probe before curing increases. In the present invention, by subjecting surface treatment on silica particles having an average primary particle diameter within the above-described specific range, an interaction between the silica particles with polyorganosiloxane and polysiloxane resin becomes stronger and the affinity increases. For this reason, it is considered that aggregation of silica particles having a small average primary particle diameter is suppressed, the viscosity of the composition for an acoustic wave probe before curing is suppressed, the tear strength of the silicone resin after curing is high, and the acoustic attenuation is decreased.

The average primary particle diameter of the ingredient (D) used in the present invention is more than 16 nm and less than 100 nm, from the viewpoint of suppressing an increase in the viscosity of a composition for an acoustic wave probe before curing, suppressing an increase in the acoustic attenuation of the silicone resin, and enhancing the tear strength. The average primary particle diameter of the ingredient (D) is preferably 17 nm or more, more preferably 18 nm or more, even more preferably 20 nm or more, and particularly preferably 25 nm or more. Furthermore, the average primary particle diameter of the ingredient (D) is preferably 98 nm or less, more preferably 90 nm or less, even more preferably 80 nm or less, and particularly preferably 70 nm or less. Furthermore, the average primary particle diameter of the ingredient (D) is preferably 18 nm to 90 nm, more preferably 20 nm to 80 nm, and even more preferably 25 nm to 70 nm.

Here, the average primary particle diameter means a volume average particle diameter. This volume average particle diameter is determined as follows.

Silica particles are added to methanol to a concentration of 0.5% by mass, the mixture is subjected to ultrasound for 10 minutes, and thereby the silica particles are dispersed. The particle diameter distribution of the particles thus treated is measured using a laser diffraction scattering type particle diameter distribution analyzer (manufactured by HORIBA, Ltd., trade name: LA950V2), and the volume-based median diameter of the particle diameter distribution is designated as the particle diameter. The median diameter corresponds to the cumulative 50% value when the particle diameter distribution is presented as a cumulative distribution.

The ingredient (D) may be used singly or in a combination of two or more thereof.

The specific surface area of the ingredient (D) used in the present invention is preferably 1 to 400 $m^2/g$, more preferably 5 to 200 $m^2/g$, and particularly preferably 10 to 100 $m^2/g$ from the viewpoint of improving at least one of the viscosity of the composition before curing and the mechanical strength of a silicone resin to be obtained.

The ingredient (D) used in the present invention is silica particles, with the surface of the particles being surface-treated. Silica particles that have been surface-treated with a silane compound are preferred because the silica particles and the silane compound are formed from similar silicon-based materials, and the hydrophilic silica surface can be efficiently subjected to hydrophobization.

A usual technique may be used as a technique of the surface treatment. Examples of the technique of the surface treatment using a silane compound include a technique of performing surface treatment using a silane coupling agent and a technique of performing coating using a silicone compound.

(i) Silane Coupling Agent

The silane coupling agent is preferably a silane coupling agent having a hydrolyzable group, from the viewpoint of improving at least one of the viscosity before curing of the composition and the mechanical strength of the silicone resin. When the hydrolyzable group in the silane coupling agent is hydrolyzed by water to become a hydroxyl group, and this hydroxyl group undergoes a dehydration condensation reaction with a hydroxyl group at the silica particle surface, the surface of the silica particles is modified, and at least one of the viscosity before curing of the composition and the mechanical strength of the silicone resin to be obtained is improved. Examples of the hydrolyzable group include an alkoxy group, an acyloxy group, and a halogen atom.

When the surface of the silica particles has been subjected to surface modification to become hydrophobic, aggregation between the silica particles is not easily achieved, the affinity between the ingredient (D) and the ingredients (A) to (C) becomes satisfactory, and the viscosity of the composition before curing and the mechanical strength of the silicone resin to be obtained are improved. Therefore, it is preferable.

The ingredient (D) is preferably surface-treated with a silane coupling agent having a hydrophobic group as a functional group. Examples of the silane coupling agent having a hydrophobic group as a functional group include alkoxysilanes such as methyltrimethoxysilane (MTMS), dimethyldimethoxysilane, phenyltrimethoxysilane, methyltriethoxysilane, dimethyldiethoxysilane, phenyltriethoxysilane, n-propyltrimethoxysilane, n-propyltriethoxysilane, hexyltrimethoxysilane, hexyl triethoxysilane, and decyltrimethoxysilane; chlorosilanes such as methyltrichlorosilane, dimethyldichlorosilane, trimethylchlorosilane, and phenyltrichlorosilane; and hexamethyldisilazane (HMDS).

In addition, examples of a silane coupling agent having a vinyl group as a functional group include alkoxysilanes such as methacryloxypropyltriethoxysilane, methacryloxypropyltrimethoxysilane, methacryloxypropylmethyldiethoxysilane, methacryloxypropylmethyldimethoxysilane, vinyltriethoxysilane, vinyltrimethoxysilane, and vinylmethyldimethoxysilane; chlorosilanes such as vinyltrichlorosilane and vinylmethyldichlorosilane; and divinyltetramethyldisilazane.

From the viewpoint of having an excellent effect of modifying the hydrophilic silica surface and being capable of making the reactivity higher and the treatment time shorter, the ingredient (D) is preferably silica particles treated with a trialkylsilylating agent, and more preferably silica particles treated with a trimethylsilylating agent.

In addition, examples of the trimethylsilylating agent include trimethylchlorosilane and hexamethyldisilazane (HMDS) described in the above-described silane coupling agent, and methyltrimethoxysilane (MTMS) and trimethylmethoxysilane.

A hydroxyl group existing on the surfaces of silica particles is covered with a trimethylsilyl group through a reaction with hexamethyldisilazane (HMDS), methyltrimethoxysilane (MTMS), trimethylmethoxysilane, and the like and the surfaces of the silica particles are hydrophobically modified.

In the present invention, the silane coupling agent may be used alone or in a combination of two or more thereof.

(ii) Silicone Compound

In the ingredient (D), a silicone compound with which the silica particles are coated may be a polymer formed through siloxane bonding.

Examples of the silicone compound include a silicone compound in which all or a part of both or one of side chains and terminals of polysiloxane has become a methyl group, a silicone compound in which a part of a side chain is a hydrogen atom, a modified silicone compound in which at least one of organic groups such as an amino group and an epoxy group is introduced into all or a part of at least one of side chains and terminals, and a silicone resin having a branched structure. The silicone compound may be either of a linear structure or a cyclic structure.

Examples of the silicone compound in which all or a part of both or one of side chains and terminals of polysiloxane has a methyl group include monomethylpolysiloxane such as polymethylhydrosiloxane (hydride terminated), polymethylhydrosiloxane (trimethylsiloxy terminated), polymethylphenylsiloxane (hydride terminated), and polymethylphenylsiloxane (trimethylsiloxy terminated); and dimethylpolysiloxanes such as dimethylpolysiloxane (hydride terminated), dimethylpolysiloxane (trimethylsiloxy terminated), and cyclic dimethylpolysiloxane.

Examples of the silicone compound in which a part of side chains is a hydrogen atom include methylhydrosiloxane-dimethylsiloxane copolymer (trimethylsiloxy terminated), methylhydrosiloxane-dimethylsiloxane copolymer (hydride terminated), polymethylhydrosiloxane (hydride terminated), polymethylhydrosiloxane (trimethylsiloxy terminated), polyethylhydrosiloxane (triethylsiloxy terminated), polyphenyl-(dimethylhydrosiloxy) siloxane (hydride terminated), methylhydrosiloxane-phenylmethylsiloxane copolymer (hydride terminated), methylhydrosiloxane-octylmethylsiloxane copolymer, and methylhydrosiloxane-octylmethylsiloxane-dimethylsiloxane terpolymer.

In addition, examples of modified silicone into which an organic group is introduced include reactive silicone into which at least one of an amino group, an epoxy group, a methoxy group, a (meth)acryloyl group, a phenol group, a carboxylic anhydride group, a hydroxy group, a mercapto group, and a carboxyl group is introduced; and non-reactive silicone modified with at least one of polyether, aralkyl, fluoroalkyl, long chain alkyl, long chain aralkyl, higher fatty acid ester, higher fatty acid amide, and polyether methoxy.

Silica particles coated with a silicone compound can be obtained through a usual method. For example, the silica particles can be obtained by mixing and stirring silica particles in dimethylpolysiloxane for a certain period of time and subsequent filtration.

In addition, in a case of using reactive modified silicone as a silicone compound, surface modification of silica particles is performed through reaction of an organic group with a hydroxyl group of the surfaces of the silica particles, and therefore, at least one of the viscosity of the composition before curing and the mechanical strength of a silicone resin to be obtained is improved.

In the present invention, for example, a commercially available silane compound can be used.

The methanol hydrophobicity of the ingredient (D) is preferably 40 to 80 mass %, more preferably 50 to 80 mass %, and still more preferably 60 to 80 mass %. Here, the larger the methanol hydrophobicity, the higher the hydrophobicity, and the smaller the methanol hydrophobicity, the higher the hydrophilicity. The methanol hydrophobicity is calculated by the method described in the examples.

In a case where the methanol hydrophobicity is within the above-described preferred ranges, it is possible to suppress decrease in acoustic sensitivity in a case where a silicone resin for an acoustic wave probe is obtained without increase in the viscosity of the composition for an acoustic wave probe before curing.

The Wardell's sphericity of a primary particle of the ingredient (D) is preferably 0.7 to 1, more preferably 0.8 to 1, and still more preferably 0.9 to 1.

Here, the "Wardell's sphericity" (refer to Chemical Engineering Handbook published by Maruzen Inc.) is an index obtained by measuring the sphericity of a particle as (diameter of circle equal to projection area of particle)/(diameter of minimum circle circumscribing projection image of particle). A particle having the index closer to 1.0 means a particle closer to a true sphere.

It is possible to use, for example, a scanning electron microscope (SEM) photograph can be used to measure the Wardell's sphericity (hereinafter, also simply referred to as sphericity). Specifically, for example, about 100 primary particles are observed using the SEM photograph, and each sphericity thereof is calculated. An average value obtained by dividing the total of the calculated sphericities by the number of observed primary particles is regarded as the sphericity.

The above-mentioned shape is a shape of the silica particles of the surface-treated state.

In a case where the Wardell's sphericity is within the above-described preferred ranges, it is considered that the acoustic sensitivity is improved because the area of the acoustic wave hitting the silica particles becomes smaller in a case where the silicone resin is irradiated with the acoustic wave. In particular, it is considered that the acoustic sensitivity is more effectively improved in a case where the shapes of the ingredient (D) are truly spherical within a specific range of the average primary particle diameter of the ingredient (D) used in the present invention.

In this specification, the "true spherical shape" also includes a slightly distorted sphere of which the Wardell's sphericity is within a range of 0.9 to 1.

Depending on production method, the silica particles are roughly classified into combustion method silica (that is, fumed silica) obtained by burning a silane compound, deflagration method silica obtained by explosively burning metallic silicon powder, wet-type silica (among which silica synthesized under alkaline conditions is referred to as precipitation method silica and silica synthesized under acidic conditions is referred to as gel method silica) obtained through a neutralization reaction with sodium silicate and mineral acid, and sol-gel method silica (so-called Stoeber method) obtained through hydrolysis of hydrocarbyloxysilane.

Preferred examples of a method for producing truly spherical silica particles include an explosion method and a sol-gel method.

The sol-gel method is a method of obtaining hydrophilic spherical silica particles essentially consisting of $SiO_2$ units by hydrolyzing and condensing a hydrocarbyloxysilane (preferably tetrahydrocarbyloxysilane) or a partial hydrolytic condensation product thereof or a combination thereof.

In addition, the hydrophobic treatment of the surfaces of the silica particles can also be carried out by introducing $R^3{}_3SiO_{1/2}$ units ($R^3$'s are the same as or different from each other and are substituted or unsubstituted monovalent hydrocarbon groups having 1 to 20 carbon atoms) onto the surfaces of hydrophilic spherical silica particles.

Specifically, the hydrophobic treatment thereof can be carried out, for example, through methods disclosed in JP-A-2007-99582 and JP-A-2014-114175.

<Other Components>

In the composition for an acoustic wave probe of the present invention, it is possible to appropriately formulate at least one of a platinum catalyst for an addition polymerization reaction, a cure retardant, a solvent, a dispersant, a pigment, a dye, an antistatic agent, an antioxidant, a flame retardant, and a thermal conductivity enhancer in addition to the ingredients (A) to (D).

—Catalyst—

Examples of the catalyst include platinum or a platinum-containing compound (hereinafter, also simply referred to as a platinum compound). Any platinum or platinum compound can be used.

Specific examples thereof include a catalyst in which platinum black or platinum is carried on an inorganic compound, carbon black, or the like; chloroplatinic acid or an alcohol solution of chloroplatinic acid; a complex salt of chloroplatinic acid and olefin; and a complex salt of chloroplatinic acid and vinyl siloxane. The catalyst may be used singly, or in a combination of two or more thereof.

The catalyst is effective for a hydrosilylation reaction in which a Si—H group is added to a vinyl group. When a hydrosilylation reaction (addition curing reaction) proceeds, an advanced three-dimensional network structure by the ingredients (A) to (C) can be made. The molar ratio of the Si—H group and the vinyl group in this hydrosilylation reaction can be determined on the basis of the stoichiometric ratio; however, the molar ratio is not limited thereto.

Here, the catalyst may be contained in the composition for an acoustic wave probe of the present invention or may be brought into contact with the composition for an acoustic wave probe without being contained in the composition for an acoustic wave probe. The latter case is preferable.

Examples of commercially available platinum catalyst include platinum compounds (a trade name of PLATINUM CYCLOVINYLMETHYLSILOXANE COMPLEX IN CYCLIC METHYLVINYLSILOXANES (SIP6832.2) with 2 mass % of Pt concentration; and a trade name of PLATINUM DIVINYLTETRAMETHYLDISILOXANE COMPLEX IN VINYL-TERMINATED POLYDIMETHYLSILOXANE (SIP6830.3) with 3 mass % of Pt concentration, all of which are manufactured by GELEST, INC.)

In a case where a catalyst is contained in the composition for an acoustic wave probe of the present invention, the content of the catalyst is not particularly limited, but is preferably 0.00001 to 0.05 parts by mass, more preferably 0.00001 to 0.01 parts by mass, still more preferably 0.00002 to 0.01 parts by mass, and particularly preferably 0.00005 to 0.005 parts by mass with respect to 100 parts by mass of the total content of the ingredients (A) to (D) from the viewpoint of reactivity.

In addition, it is possible to control the curing temperature by selecting an appropriate platinum catalyst. For example, platinum-vinyldisiloxane is used for room temperature vulcanization (RTV) at lower than or equal to 50° C. and platinum-cyclic vinylsiloxane is used for high temperature vulcanization (HTV) at higher than or equal to 130° C.

—Cure Retardant—

In the present invention, a cure retardant for curing reaction can be appropriately used. The cure retardant is used for delaying the above-described addition curing reaction and examples thereof include a low molecular weight vinylmethylsiloxane homopolymer (trade name: VMS-005 manufactured by GELEST, INC.)

The curing rate, that is, the working time can be adjusted depending on the content of the cure retardant.

[Viscosity of Composition for Acoustic Wave Probe Before Curing]

The viscosity of the composition for an acoustic wave probe before performing a curing reaction is preferably low. In a case where the viscosity is too high, it becomes difficult to prepare a composition for an acoustic wave probe in which the ingredient (D) are dispersed through kneading. The viscosity of the composition for an acoustic wave probe before adding a catalyst which initiates the cure reaction is measured in order to measure the viscosity before curing. Specifically, the viscosity at 23° C. is measured by the method described in the Examples.

The viscosity (23° C.) is preferably 5,000 Pa·s or less, more preferably 1,000 Pa·s or less, and particularly preferably 200 Pa·s or less. The actual lower limit is 10 Pa·s or greater.

When the viscosity is within the above-described preferred range, it is easy to handle the composition for an acoustic wave probe at the time of processing. Furthermore, since residual air bubbles in the composition for an acoustic wave probe can be suppressed, an increase in the acoustic attenuation, which is attributed to the air bubbles present in the silicone resin for an acoustic wave probe, can also be suppressed.

<Method for Producing Composition for Acoustic Wave Probe and Silicone Resin for Acoustic Wave Probe>

The composition for an acoustic wave probe of the present invention can be produced through an ordinary method.

For example, the composition for an acoustic wave probe can be obtained by kneading components constituting the composition for an acoustic wave probe using a kneader, a pressure kneader, a Banbury mixer (continuous kneader), and a kneading device with two rolls. The order of mixing the components is not particularly limited.

It is preferable to first make a polyorganosiloxane mixture in which the ingredient (D) are dispersed in the ingredients (A) to (C), from the viewpoint of obtaining a homogeneous composition. Thereafter, it is possible to produce a composition for an acoustic wave probe by adding a catalyst to the polysiloxane mixture, in which the ingredient (D) are dispersed, and then performing defoamation under reduced pressure.

The kneading conditions of the polyorganosiloxane mixture in which the ingredient (D) is dispersed are not particularly limited as long as the ingredients (D) is dispersed. For example, the polyorganosiloxane mixture is preferably kneaded at 10° C. to 50° C. for 1 to 72 hours.

It is possible to obtain a silicone resin for an acoustic wave probe of the present invention by curing the composition for an acoustic wave probe of the present invention which is obtained in this manner. Specifically, it is possible to obtain a silicone resin for an acoustic wave probe by, for example, thermally curing the composition for an acoustic wave probe for 5 minutes to 500 minutes at 20° C. to 200° C.

The composition for an acoustic wave probe of the present invention is useful for medical members and can preferably be used, for example, in an acoustic wave probe and an acoustic wave measurement apparatus. The acoustic wave measurement apparatus of the present invention is not limited to an ultrasound diagnostic apparatus or a photoacoustic wave measurement apparatus, and is referred to as an apparatus that receives an acoustic wave which is reflected or generated from an object and displays the received acoustic wave as an image or a signal strength.

Particularly, the composition for an acoustic wave probe of the present invention can suitably be used in: an acoustic lens of a probe for an ultrasound diagnostic apparatus; a material of an acoustic matching layer which is provided between a piezoelectric element and the acoustic lens and plays a role of matching acoustic impedance between the piezoelectric element and the acoustic lens; a material of an acoustic lens in a photoacoustic wave measurement apparatus or an ultrasound endoscope; a material of an acoustic lens in an ultrasound probe including capacitive micromachined ultrasonic transducers (cMUT) as an ultrasonic transducer array; or the like.

Specifically, the silicone resin for an acoustic wave probe of the present invention is preferably applied to, for example, an ultrasound diagnostic apparatus described in JP-A-2005-253751, JP-A-2003-169802, and the like and an acoustic wave measurement apparatus such as a photoacoustic wave measurement apparatus described in JP-A-2013-202050, JP-A-2013-188465, JP-A-2013-180330, JP-A-2013-158435, JP-A-2013-154139, and the like.

<<Acoustic Wave Probe (Probe)>>

A configuration of an acoustic wave probe of the present invention will be described below in more detail based on a configuration of an ultrasound probe in an ultrasound diagnostic apparatus which is described in the FIGURE. The ultrasound probe is a probe which particularly uses an ultrasonic wave as an acoustic wave in an acoustic wave probe. For this reason, a basic configuration of the ultrasound probe can be applied to the acoustic wave probe as it is.

—Ultrasound Probe—

An ultrasound probe 10 is a main component of the ultrasound diagnostic apparatus and has a function of generating an ultrasonic wave and transmitting and receiving an ultrasonic beam. The configuration of the ultrasound probe 10 is provided in the order of an acoustic lens 1, an acoustic matching layer 2, a piezoelectric element layer 3, and a backing material 4 from a distal end (the surface coming into contact with a living body which is a test object) as shown in the FIGURE. In recent years, an ultrasound probe having a laminated structure in which an ultrasonic transducer (piezoelectric element) for transmission and an ultrasonic transducer (piezoelectric element) for reception are formed of materials different from each other has been proposed in order to receive high-order harmonics.

<Piezoelectric Element Layer>

The piezoelectric element layer 3 is a portion which generates an ultrasonic wave and in which an electrode is attached to both sides of a piezoelectric element. In a case where voltage is applied to the electrode, the piezoelectric element layer generates an ultrasonic wave through repeated contraction and expansion of the piezoelectric element and through vibration.

Inorganic piezoelectric bodies of so-called ceramics obtained by polarizing crystals, single crystals such as $LiNbO_3$, $LiTaO_3$, and $KNbO_3$, thin films of ZnO AlN, or the like, $Pb(Zr,Ti)O_3$-based sintered body, and the like are widely used as the material constituting a piezoelectric element. In usual, piezoelectric ceramics such as lead zirconate titanate (PZT) with good conversion efficiency are used.

In addition, sensitivity having a wider band width is required for a piezoelectric element detecting a reception wave on a high frequency side. For this reason, an organic piezoelectric body has been used in which an organic polymer material such as polyvinylidene fluoride (PVDF) is used as the piezoelectric element being suitable for a high frequency or a wide band.

Furthermore, cMUT using micro electro mechanical systems (MEMS) technology in which an array structure, which shows excellent short pulse characteristics, excellent broadband characteristics, and excellent mass productivity and has less characteristic variations, is obtained is described in JP-A-2011-071842 or the like.

In the present invention, it is possible to preferably use any piezoelectric element material.

<Backing Material>

The backing material 4 is provided on a rear surface of the piezoelectric element layer 3 and contributes to the improvement in distance resolution in an ultrasonic diagnostic image by shortening the pulse width of an ultrasonic wave through the suppression of excess vibration.

<Acoustic Matching Layer>

The acoustic matching layer 2 is provided in order to reduce the difference in acoustic impedance between the piezoelectric element layer 3 and a test object and to efficiently transmit and receive an ultrasonic wave.

Since the composition for an ultrasound probe of the present invention has an acoustic impedance that is different from the acoustic impedance of a living body ($1.4 \times 10^6$ to $1.7 \times 10^6$ $kg/m^2/sec$) to a small extent or is within this range, the composition for an ultrasound probe can be preferably used as a material for an acoustic matching layer. It is preferable that the acoustic matching layer in the acoustic wave probe of the present invention contains a silicone resin for an acoustic wave probe, which is obtained by subjecting the composition for an acoustic wave probe of the present invention to a curing reaction, at a proportion of 10% by mass or more.

<Acoustic Lens>

The acoustic lens 1 is provided in order to improve resolution by making an ultrasonic wave converge in a slice direction using refraction. In addition, it is necessary for the acoustic lens to achieve matching of an ultrasonic wave with acoustic impedance ($1.4 \times 10^6$ to $1.7 \times 10^6$ $kg/m^2/sec$ in a case of a human body) of a living body which is a test object after being closely attached to the living body and to reduce ultrasonic attenuation of the acoustic lens 1 itself.

That is, sensitivity of transmission and reception of an ultrasonic wave is improved using a material of which the acoustic velocity is sufficiently lower than that of a human body, the ultrasound attenuation is low, and the acoustic impedance is close to a value of the skin of a human body, as the material of the acoustic lens 1.

The composition for an acoustic wave probe as a composition for an ultrasound probe of the present invention can also preferably be used as a material of the acoustic lens.

The operation of the ultrasound probe 10 having such a configuration will be described. The piezoelectric element layer 3 is resonated by applying voltage to the electrodes provided on both sides of a piezoelectric element, and an ultrasound signal is transmitted to a test object from the acoustic lens. During reception of the ultrasonic signal, the piezoelectric element layer 3 is vibrated using the signal (echo signal) reflected from the test object and this vibration is electrically converted into a signal to obtain an image.

Particularly, a remarkable effect of improving the sensitivity can be checked from a transmission frequency of an ultrasonic wave of greater than or equal to about 5 MHz using the acoustic lens obtained from the composition for an ultrasound probe of the present invention as a usual medical ultrasonic transducer. Particularly, a remarkable effect of improving the sensitivity can particularly be expected from a transmission frequency of an ultrasonic wave of greater than or equal to 10 MHz.

Hereinafter, an apparatus in which the acoustic lens obtained from the composition for an ultrasound probe of the present invention exhibits a function particularly regarding conventional problems will be described in detail.

The composition for an ultrasound probe of the present invention exhibits an excellent effect even with respect to other apparatuses described below.

—Ultrasound Probe Including Capacitive Micromachined Ultrasonic Transducer (cMUT)—

In a case where cMUT apparatuses described in JP-A-2006-157320, JP-A-2011-71842, and the like are used in an ultrasonic diagnostic transducer array, the sensitivity thereof usually becomes low compared to a transducer in which usual piezoelectric ceramics (PZT) is used.

However, it is possible to make up for deficient sensitivity of cMUT using the acoustic lens obtained from the composition for an acoustic wave probe of the present invention. Accordingly, it is possible to make the sensitivity of cMUT to performance of a conventional transducer.

The cMUT device is manufactured through MEMS technology. Therefore, it is possible to provide an inexpensive ultrasound probe, of which mass productivity is higher than that of a piezoelectric ceramics probe, to the market.

—Photoacoustic Wave Measurement Apparatus Using Photo-Ultrasound Imaging—

Photoultrasound imaging (photo acoustic imaging: PAI) described in JP-A-2013-158435 or the like displays a signal strength of an ultrasonic wave or an image obtained by imaging the ultrasonic wave generated in a case where human tissue is adiabatically expanded using light (magnetic wave) with which the interior of a human body is irradiated.

Here, the amount of an acoustic pressure of an ultrasonic wave generated through light irradiation is minute, and therefore, there is a problem in that it is difficult to observe deeper regions of a human body.

However, it is possible to exhibit an effect effective for the problem using the acoustic lens obtained from the composition for an acoustic wave probe of the present invention.

—Ultrasound Endoscope—

In an ultrasonic wave in an ultrasound endoscope described in JP-A-2008-311700 or the like, a signal line cable is structurally long compared to that of a transducer for a body surface, and therefore, there is a problem of improving the sensitivity of the transducer accompanied by loss of the cable. Regarding this problem, it is said that there are no effective means for improving the sensitivity due to the following reasons.

First, in a case of an ultrasound diagnostic apparatus for a body surface, it is possible to install an amplifier circuit, an AD conversion IC, or the like at a distal end of the transducer. In contrast, the ultrasound endoscope is inserted into a body. Therefore, there is a small installation space within the transducer, and thus, it is difficult to install the amplifier circuit, the AD conversion IC, or the like at a distal end of the transducer.

Secondly, it is difficult to apply a piezoelectric single crystal employed in the transducer in the ultrasound diagnostic apparatus for a body surface onto a transducer with an ultrasonic transmission frequency of greater than or equal to 7 to 8 MHz due to physical properties and processing suitability. However, an ultrasonic wave for an endoscope is usually a probe having an ultrasonic transmission frequency of greater than or equal to 7 to 8 MHz, and therefore, it is also difficult to improve the sensitivity using piezoelectric single crystal material.

However, it is possible to improve the sensitivity of the ultrasonic transducer for an endoscope using the acoustic lens obtained from the composition for an acoustic wave probe of the present invention.

In addition, even in a case of using the same ultrasonic transmission frequency (for example, 10 MHz), the efficacy is particularly exhibited in a case of using the acoustic lens obtained from the composition for an acoustic wave probe of the present invention in the ultrasonic transducer for an endoscope.

EXAMPLES

Hereinafter, the present invention will be described in more detail based on Examples in which an ultrasonic wave is used as an acoustic wave. The present invention is not limited to the ultrasonic wave, and any acoustic wave of an audible frequency may be used as long as an appropriate frequency is selected in accordance with a test object, measurement conditions, and the like.

(Polysiloxane Resin (the Ingredient (C) in Table 1 Below))

Hereinafter, polysiloxane resins which were used in Examples and Comparative Examples are shown.

Polysiloxane Resin (C-1) (referred to JP-A-2014-80546)

Polysiloxane resin represented by the following average composition formula (M/Q=0.87)

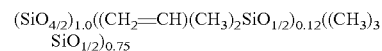

The kinematic viscosity of the 50% by mass xylene solution of the polysiloxane resin (C-1) was 3.0 mm$^2$/s.

Polysiloxane Resin (C-2) (referred to JP-A-2014-80546)

Polysiloxane resin represented by the following average composition formula (M/Q=1.75)

The kinematic viscosity of the 50% by mass xylene solution of the polysiloxane resin (C-2) was 1.5 mm$^2$/s.

Polysiloxane Resin (C-3) (JP-A-H-7-331079)

Polysiloxane resin represented by the following average composition formula (M/Q=1.06)

The kinematic viscosity of the 50% by mass xylene solution of the polysiloxane resin (C-3) was 3.5 mm$^2$/s.

Polysiloxane Resin (C-4)

Polysiloxane resin represented by the following average composition formula (M/Q=0.62)

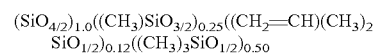

The kinematic viscosity of the 50% by mass xylene solution of the polysiloxane resin (C-4) was 3.3 mm$^2$/s.

Preparation Example of Surface-Treated Silica Particles

Surface-treated silica D-1, D-2, T-1, and T-2 having the average primary particle diameters, the methanol hydrophobicity degree, and truly spherical shape described in the following Table 1 were respectively obtained in the same manner as the example described in Synthesis Example 1 of JP-A-2007-99582, except that the amounts of methanol, water, and 28% aqueous ammonia in step (A1) were changed.

Example 1

44.0 parts by mass of a vinyl terminated diphenylsiloxane-dimethylsiloxane copolymer ("PDV-0535" (trade name) manufactured by GELEST, INC. with a mass average molecular weight of 47,500 and a diphenylsiloxane amount of 5 mol %), 1.0 parts by mass of polymethylhydrosiloxane ("HMS-991" (trade name) manufactured by GELEST, INC. with a mass average molecular weight of 1,600), 10.0 parts by mass of polysiloxane resin (C-1), and 45.0 parts by mass of truly spherical surface-treated silica ("QSG-30" (trade name) manufactured by Shin-Etsu Chemical Co., Ltd. with an average primary particle diameter of 30 nm which was a surface-treated product with methyltrimethoxysilane (MTMS) and hexamethyldisilazane (HMDS) and had a methanol hydrophobicity degree of 67%) were kneaded with a kneader for 2 hours (temperature of 25° C.) to obtain a homogeneous paste. 0.05 parts by mass of a platinum catalyst solution (manufactured by GELEST, INC., trade name of "SIP6821.3" (trade name) with 3 mass % of Pt concentration) was added to and mixed with the paste. Then, the mixture was subjected to defoamation under reduced pressure, placed in a metal mold of length of 150 mm×width of 150 mm×depth of 1 mm, and subjected to heat treatment for 3 hours at 60° C. to produce a silicone resin for an acoustic wave probe (sheet of length of 150 mm×width of 150 mm×thickness of 2 mm). A silicone resin sheet having length of 150 mm×width of 150 mm×thickness of 2 mm was prepared in the same manner except that a metal mold having a length of 150 mm×width of 150 mm×depth of 2 mm was used. Hereinafter, the silicone resin for an acoustic wave probe produced in this manner is referred to as a "silicone resin sheet".

Examples 2 to 20, Comparative Examples 1 and 3 to 6

Predetermined silicone resin sheets were produced in the same manner as Example 1, except that the composition of the polysiloxane composition of Example 1 was changed to the compositions described in the following Table 1. The platinum catalyst solution was used in the same amount as that of Example 1 in all cases.

Comparative Example 2

44.0 parts by mass of a vinyl terminated diphenylsiloxane-dimethylsiloxane copolymer ("PDV-0535" manufactured by GELEST, INC. with a mass average molecular weight of 47,500 and a diphenylsiloxane amount of 5 mol %), 1.0 parts by mass of polymethylhydrosiloxane ("HMS-991" manufactured by GELEST, INC. with a mass average molecular weight of 1,600), 10.0 parts by mass of polysiloxane resin (C-1), and 45.0 parts by mass of heteromorphic surface-treated fumed silica ("AEROSIL (registered trademark) R974 (trade name) manufactured by NIPPON AEROSIL CO., LTD. with an average primary particle diameter of 12 nm which was a surface-treated product with dimethyldichlorosilane (DDS) and had a methanol hydrophobicity of 33 mass %) were kneaded with a kneader for 2 hours at a set temperature of 23° C. However, since the viscosity was too high, the kneader overloaded and stopped. Therefore, it was impossible to knead the mixture.

Comparative Example 7

44.0 parts by mass of a vinyl terminated diphenylsiloxane-dimethylsiloxane copolymer ("PDV-0535" manufactured by GELEST, INC. with a mass average molecular weight of 47,500 and a diphenylsiloxane amount of 5 mol %), 1.0 parts by mass of polymethylhydrosiloxane ("HMS-991" manufactured by GELEST, INC. with a mass average molecular weight of 1,600), 10.0 parts by mass of polysiloxane resin (C-1), and 45.0 parts by mass of heteromorphic non-treated fumed silica ("AEROSIL (registered trademark) 50 (trade name) manufactured by NIPPON AEROSIL CO., LTD. with an average primary particle diameter of 30 nm without surface treatment which had a methanol hydrophobicity of 0 mass %) were kneaded with a kneader for 2 hours at a set temperature of 23° C. However, since the viscosity was too high, the kneader overloaded and stopped. Therefore, it was impossible to knead the mixture.

[Methanol Hydrophobicity]

50 ml of ion exchange water and 0.2 g of silica particles as samples were placed in a beaker at 25° C. and stirred with a magnetic stirrer, methanol was added dropwise thereto from a burette, and the amount (Xg) of methanol added dropwise until the whole sample settles was measured. The methanol hydrophobicity was calculated using the following equation.

Methanol hydrophobicity (mass %)=$X/(50+X) \times 100$

[Viscosity Before Curing]

The viscosity of a paste before addition of a platinum catalyst was measured using "RheoStress RS6000" which is a trade name manufactured by HAAKE under the conditions of a temperature of 23° C. and a shear rate of 0.001 s$^{-1}$, and evaluated according to the following evaluation criteria.

In Comparative Examples 2 and 7, it was impossible to obtain a homogeneous composition due to high viscosity, and therefore, it was impossible to measure the viscosity.

—Evaluation Criteria—

A: less than 1,000 Pa·s

B: 1,000 Pa·s or more and less than 10,000 Pa·s

C: 10,000 Pa·s or more and less than 100,000 Pa·s

D: 100,000 Pa·s or more

A and B are acceptable.

<Evaluation of Mechanical Strength and Ultrasonic Characteristics>

The following evaluation was performed on silicone resin sheets of Examples 1 to 20, Comparative Examples 1 and 3 to 6.

[Tear Strength Test]

A trouser-type test piece of a silicone resin sheet with a thickness of 2 mm was manufactured and the tear strength was measured in compliance with JIS K6252 (2007), and evaluated according to the following evaluation criteria.

—Evaluation Criteria—

A: 40 N/cm or more

B: 20 N/cm or more and less than 40 N/cm

C: 10 N/cm or more and less than 20 N/cm

D: less than 10 N/cm

A, B and C are acceptable.

[Abrasion Resistance Test (DIN Abrasion Test)]

For a silicone resin sheet having a thickness of 1 mm, an abrasion resistance test was carried out according to JIS K 6264-2 (2005). As a DIN abrasion testing machine, trade name: "No. 151 DIN abrasion testing machine" manufactured by YASUDA SEIKI SEISAKUSHO, LTD., was used.

Specifically, the DIN abrasion amount was measured under a load of 10 N at a speed of drum rotation of 40 rpm and an abrasion distance of 40 m, and the DIN abrasion amount was evaluated on the basis of the following evaluation criteria. The values in the following evaluation criteria are relative values obtainable when the value of Comparative Example 3 for the reciprocal of the DIN abrasion amount was designated as 100%. As the value is larger, the abrasion amount is smaller, and the abrasion resistance is satisfactory.

—Evaluation Criteria—

A: 110% or more

B: 105% or more and less than 110%

C: 100% or more and less than 105%

D: less than 100%

A, B and C are acceptable.

[Acoustic Impedance]

The density of each of the obtained silicone resin sheets with a thickness of 2 mm at 25° C. was measured using an electronic gravimeter (a trade name of "SD-200L" manufactured by ALFA MIRAGE) in accordance with a density measurement method of a method A (underwater substitution method) disclosed in JIS K7112 (1999). The acoustic velocity of an ultrasonic wave was measured at 25° C. using a sing-around type acoustic velocity measurement apparatus (a trade name of "UVM-2 type" manufactured by Ultrasonic Engineering Co., Ltd.) in compliance with JIS Z2353 (2003) and acoustic impedance was obtained from a sum of the density and the acoustic velocity which had been measured, and evaluated according to the following evaluation criteria.
—Evaluation Criteria—
A: $1.35 \times 10^6$ kg/m²/s or more
B: $1.27 \times 10^6$ kg/m²/s or more and less than $1.35 \times 10^6$ kg/m²/s
C: $1.20 \times 10^6$ kg/m²/s or more and less than $1.27 \times 10^6$ kg/m²/s
D: less than $1.20 \times 10^6$ kg/m²/s
A and B are acceptable.

[Acoustic (Ultrasonic) Sensitivity]

A sinusoidal signal (a wave) of 5 MHz which had been output from an ultrasound oscillator (a function generator with a trade name of "FG-350" manufactured by IWATSU ELECTRIC CO., LTD.) was input into an ultrasound probe (manufactured by JAPAN PROBE), and an ultrasound pulse wave with a center frequency of 5 MHz was generated in water from the ultrasound probe. The magnitude of the amplitude before and after the generated ultrasonic wave passed through each of the obtained silicone resin sheet with a thickness of 2 mm was measured in a water temperature environment of 25° C. using an ultrasound receiver (an oscilloscope with a trade name of "VP-5204A" manufactured by Matsushita Electric Industrial Co., Ltd.). According to the following criteria, the acoustic (ultrasonic) attenuation of each material was compared with each other by comparing the acoustic (ultrasonic) sensitivities of each material.

The acoustic (ultrasonic) sensitivity is a numerical value given by the following calculation equation.

In the following calculation equation, Vin represents a voltage peak value of an input wave which is generated by the ultrasound oscillator and has a half-width of less than or equal to 50 nsec. Vs represents a voltage value obtained when the ultrasound oscillator receives an acoustic wave (ultrasonic wave) reflected from one side of the sheet opposite to the side from which an acoustic wave (ultrasonic wave) generated enters and passes through the sheet.

Acoustic (Ultrasonic) sensitivity=20×Log (Vs/Vin)

—Evaluation Criteria—
A: −70 dB or more
B: less than −70 dB and −71 dB or more
C: less than −71 dB and −72 dB or more
D: less than −72 dB
A and B are acceptable.

The obtained results were summarized and shown in Table 1.

In table 1, the mass average molecular weight of the polyorganosiloxane (A) and the polyorganosiloxane (B) is simply described as a molecular weight, and the type of each component is indicated by a trade name.

TABLE 1

| | | | Example 1 | Example 2 | Example 3 | Example 4 | Example 5 | Example 6 | Example 7 | Example 8 |
|---|---|---|---|---|---|---|---|---|---|---|
| Composition | Ingredient (A) | Type | PDV-0535 | PDV-0541 | DMS-V52 | DMS-V46 | DMS-V42 | DMS-V41 | DMS-V31 | PDV-0535 |
| | | Molecular weight | 47,500 | 60,000 | 155,000 | 117,000 | 72,000 | 62,700 | 28,000 | 47,500 |
| | | Content [mass %] | 44.0 | 44.2 | 44.7 | 44.6 | 44.5 | 44.4 | 43.5 | 44.0 |
| | Ingredient (B) | Type | HMS-991 | HMS-991 | HMS-991 | HMS-991 | HMS-991 | HMS-991 | HMS-991 | HMS-991 |
| | | Molecular weight | 1,600 | 1,600 | 1,600 | 1,600 | 1,600 | 1,600 | 1,600 | 1,600 |
| | | Content [mass %] | 1.0 | 0.8 | 0.3 | 0.4 | 0.5 | 0.6 | 1.5 | 1.0 |
| | Ingredient (C) | Type | C-1 | C-1 | C-1 | C-1 | C-1 | C-1 | C-1 | C-2 |
| | | Content [mass %] | 10.0 | 10.0 | 10.0 | 10.0 | 10.0 | 10.0 | 10.0 | 10.0 |
| | Ingredient (D) | Type | QSG-30 | QSG-30 | QSG-30 | QSG-30 | QSG-30 | QSG-30 | QSG-30 | QSG-30 |
| | | Average primary particle diameter [nm] | 30 | 30 | 30 | 30 | 30 | 30 | 30 | 30 |
| | | Shape | Truly spherical shape | Truly spherical shape | Truly spherical shape | Truly spherical shape | Truly spherical shape | Truly spherical shape | Truly spherical shape | Truly spherical shape |
| | | Methanol hydrophobicity [%] | 67 | 67 | 67 | 67 | 67 | 67 | 67 | 67 |
| | | Content [mass %] | 45.0 | 45.0 | 45.0 | 45.0 | 45.0 | 45.0 | 45.0 | 45.0 |
| Evaluation | Viscosity before curing | | A | A | A | A | A | A | A | A |
| | Tear strength | | A | A | A | A | A | A | C | A |
| | Abrasion resistance | | A | A | B | B | B | B | B | B |
| | Acoustic impedance | | A | A | B | B | B | B | B | A |
| | Acoustic (ultrasonic) Sensitivity | | A | A | A | A | A | A | A | B |

| | | | Example 9 | Example 10 | Example 11 | Example 12 | Example 13 | Example 14 | Example 15 |
|---|---|---|---|---|---|---|---|---|---|
| Composition | Ingredient (A) | Type | PDV-0535 | PDV-0535 | PDV-0535 | PDV-0535 | PDV-0535 | PDV-0535 | PDV-0535 |
| | | Molecular weight | 47,500 | 47,500 | 47,500 | 47,500 | 47,500 | 47,500 | 47,500 |
| | | Content [mass %] | 44.0 | 44.0 | 48.0 | 37.0 | 59.0 | 29.0 | 44.0 |
| | Ingredient (B) | Type | HMS-991 | HMS-991 | HMS-991 | HMS-991 | HMS-991 | HMS-991 | HMS-991 |
| | | Molecular weight | 1,600 | 1,600 | 1,600 | 1,600 | 1,600 | 1,600 | 1,600 |
| | | Content [mass %] | 1.0 | 1.0 | 1.0 | 1.0 | 1.0 | 1.0 | 1.0 |
| | Ingredient (C) | Type | C-3 | C-4 | C-1 | C-1 | C-1 | C-1 | C-1 |
| | | Content [mass %] | 10.0 | 10.0 | 6.0 | 17.0 | 10.0 | 10.0 | 10.0 |
| | Ingredient (D) | Type | QSG-30 | QSG-30 | QSG-30 | QSG-30 | QSG-30 | QSG-30 | QSG-80 |
| | | Average primary particle diameter [nm] | 30 | 30 | 30 | 30 | 30 | 30 | 80 |

TABLE 1-continued

|  |  |  | | | | | | | |
|---|---|---|---|---|---|---|---|---|---|
|  |  | Shape | Truly spherical shape | Truly spherical shape | Truly spherical shape | Truly spherical shape | Truly spherical shape | Truly spherical shape | Truly spherical shape |
|  |  | Methanol hydrophobicity [%] | 67 | 67 | 67 | 67 | 67 | 67 | 67 |
|  |  | Content [mass %] | 45.0 | 45.0 | 45.0 | 45.0 | 30.0 | 60.0 | 45.0 |
| Evaluation | Viscosity before curing |  | A | A | A | A | A | B | A |
|  | Tear strength |  | A | B | B | A | C | A | B |
|  | Abrasion resistance |  | A | C | C | A | A | C | A |
|  | Acoustic impedance |  | A | A | A | A | B | A | A |
|  | Acoustic (ultrasonic) sensitivity |  | A | B | A | B | A | B | B |

|  |  |  | Example 16 | Example 17 | Example 18 | Example 19 | Example 20 |
|---|---|---|---|---|---|---|---|
| Composition | Ingredient (A) | Type | PDV-0535 | PDV-0535 | PDV-0535 | PDV-0535 | PDV-0535 |
|  |  | Molecular weight | 47,500 | 47,500 | 47,500 | 47,500 | 47,500 |
|  |  | Content [mass %] | 44.0 | 44.0 | 44.0 | 44.0 | 44.0 |
|  | Ingredient (B) | Type | HMS-991 | HMS-991 | HMS-991 | HMS-991 | HMS-991 |
|  |  | Molecular weight | 1,600 | 1,600 | 1,600 | 1,600 | 1,600 |
|  |  | Content [mass %] | 1.0 | 1.0 | 1.0 | 1.0 | 1.0 |
|  | Ingredient (C) | Type | C-1 | C-1 | C-1 | C-1 | C-1 |
|  |  | Content [mass %] | 10.0 | 10.0 | 10.0 | 10.0 | 10.0 |
|  | Ingredient (D) | Type | YA050C-SP3 | MSP-011 | NAX50 | D-1 | D-2 |
|  |  | Average primary particle diameter [nm] | 50 | 30 | 30 | 18 | 97 |
|  |  | Shape | Truly spherical shape | Heteromorphic shape | Heteromorphic shape | Truly spherical shape | Truly spherical shape |
|  |  | Methanol hydrophobicity [%] | 47 | 41 | 28 | 61 | 76 |
|  |  | Content [mass %] | 45.0 | 45.0 | 45.0 | 45.0 | 45.0 |
| Evaluation | Viscosity before curing |  | B | B | B | B | A |
|  | Tear strength |  | B | B | C | A | C |
|  | Abrasion resistance |  | A | B | B | A | B |
|  | Acoustic impedance |  | A | A | A | A | A |
|  | Acoustic (ultrasonic) sensitivity |  | A | B | B | B | B |

|  |  |  | CEx 1 | CEx 2 | CEx 3 | CEx 4 | CEx 5 | CEx 6 | CEx 7 |
|---|---|---|---|---|---|---|---|---|---|
| Composition | Ingredient (A) | Type | PDV-0535 | PDV-0535 | PDV-0535 | PDV-0535 | PDV-0535 | PDV-0535 | PDV-0535 |
|  |  | Molecular weight | 47,500 | 47,500 | 47,500 | 47,500 | 47,500 | 47,500 | 47,500 |
|  |  | Content [mass %] | 54.0 | 44.0 | 68.5 | 44.0 | 44.0 | 44.0 | 44.0 |
|  | Ingredient (B) | Type | HMS-991 | HMS-991 | HMS-991 | HMS-991 | HMS-991 | HMS-991 | HMS-991 |
|  |  | Molecular weight | 1,600 | 1,600 | 1,600 | 1,600 | 1,600 | 1,600 | 1,600 |
|  |  | Content [mass %] | 1.0 | 1.0 | 1.5 | 1.0 | 1.0 | 1.0 | 1.0 |
|  | Ingredient (C) | Type | — | C-1 | C-1 | C-1 | C-1 | C-1 | C-1 |
|  |  | Content [mass %] |  | 10.0 | 10.0 | 10.0 | 10.0 | 10.0 | 10.0 |
|  | Ingredient (D) | Type | QSG-30 | R974 | R974 | T-1 | T-2 | QSG-100 | 50 |
|  |  | Average primary particle diameter [nm] | 30 | 12 | 12 | 16 | 104 | 110 | 30 |
|  |  | Shape | Truly spherical shape | Heteromorphic shape | Heteromorphic shape | Truly spherical shape | Truly spherical shape | Truly spherical shape | Heteromorphic shape |
|  |  | Methanol hydrophobicity [%] | 67 | 33 | 33 | 59 | 70 | 67 | 0 |
|  |  | Content [mass %] | 45.0 | 45.0 | 20.0 | 45.0 | 45.0 | 45.0 | 45.0 |
| Evaluation | Viscosity before curing |  | A | Kneading could not be performed since viscosity was too high. | D | C | A | A | Kneading could not be performed since viscosity was too high. |
|  | Tear strength |  | B |  | B | A | D | D |  |
|  | Abrasion resistance |  | D |  | C | A | C | C |  |
|  | Acoustic impedance |  | A |  | D | A | A | A |  |
|  | Acoustic (ultrasonic) sensitivity |  | A |  | D | D | C | D |  |

CEx: Comparative Example
<Notes of Table>
[Ingredient (A)]
PDV-0535: trade name, vinyl terminated diphenylsiloxane-dimethylsiloxane copolymer manufactured by GELEST, INC., mass average molecular weight of 47,500, diphenylsiloxane amount of 5 mol %
PDV-0541: trade name, vinyl terminated diphenylsiloxane-dimethylsiloxane copolymer manufactured by GELEST, INC., mass average molecular weight of 60,000, diphenylsiloxane amount of 5 mol %
DMS-V52: trade name, vinyl terminated polydimethylsiloxane manufactured by GELEST, INC., mass average molecular weight of 155,000
DMS-V46: trade name, vinyl terminated polydimethylsiloxane manufactured by GELEST, INC., mass average molecular weight of 117,000
DMS-V42: trade name, vinyl terminated polydimethylsiloxane manufactured by GELEST, INC., mass average molecular weight of 72,000
DMS-V41: trade name, vinyl terminated polydimethylsiloxane manufactured by GELEST, INC., mass average molecular weight of 62,700
DMS-V31: trade name, vinyl terminated polydimethylsiloxane manufactured by GELEST, INC., mass average molecular weight of 28,000
[Ingredient (B)]
HMS-991: trade name, methylhydrosiloxane polymer manufactured by GELEST, INC., mass average molecular weight of 1,600
[Ingredient (D)]
True spherical shape: having Wardell's sphericity of 0.9 to 1

TABLE 1-continued

Heteromorphic shape: having Wardell's sphericity of less than 0.9
QSG-30: trade name manufactured by Shin-Etsu Chemical Co., Ltd., average primary particle diameter of 30 nm, surface-treated product with methyltrimethoxysilane (MTMS) and hexamethyldisilazane (HMDS), true spherical shape, methanol hydrophobicity of 67%
QSG-80: trade name manufactured by Shin-Etsu Chemical Co., Ltd., average primary particle diameter of 80 nm, surface-treated product with MTMS and HMDS, true spherical shape, methanol hydrophobicity of 67%
YA050C-SP3: manufactured by Admatechs, average primary particle diameter of 50 nm, surface-treated product with phenyltrimethoxysilane, true spherical shape, methanol hydrophobicity of 47%
MSP-011: manufactured by TAYCA, average primary particle diameter of 30 nm, surface-treated product with MTMS and HMDS, heteromorphic shape, methanol hydrophobicity of 41%
AEROSIL NAX50 (NAX50 in Table 1): trade name manufactured by NIPPON AEROSIL CO., LTD., average primary particle diameter of 30 nm, fumed silica, surface-treated product with HMDS, heteromorphic shape, methanol hydrophobicity of 28%
AEROSIL R974 (R974 in Table 1): manufactured by NIPPON AEROSIL CO., LTD., average primary particle diameter of 12 nm, surface-treated product with dimethyldichlorosilane, heteromorphic shape, methanol hydrophobicity of 33%
QSG-100: trade name manufactured by Shin-Etsu Chemical Co., Ltd., average primary particle diameter of 110 nm, surface-treated product with MTMS and HMDS, methanol hydrophobicity of 67%
AEROSIL 50 (50 in Table 1): trade name, manufactured by NIPPON AEROSIL CO., LTD., average primary particle diameter of 30 nm, no surface treatment, heteromorphic shape, methanol hydrophobicity of 0%
D-1, D-2, T-1, T-2: Silica particles synthesized above
[Other]
">100 (Examples 3, 4 and 13)" means that the tear strength is greater than 100 N/cm.

As is obvious from Table 1, since the silicone resin of Comparative Example 1 does not contain the ingredient (C), the silicone resin had low abrasion resistance. Since silica particles having an average primary particle diameter of 12 nm were used, in Comparative Example 2, the viscosity of the composition for an acoustic wave probe before curing was too high, and the composition could not be kneaded. Furthermore, in Comparative Example 3 in which the content of the silica particles in Comparative Example 2 was reduced, although kneading could be performed, dispersing could not be finished, and the silicone resin had inferior acoustic wave sensitivity and insufficient acoustic impedance. In Comparative Example 4, since silica particles having an average primary particle diameter of 16 nm were used, the acoustic wave sensitivity was unacceptable. In Comparative Examples 5 and 6, since silica particles having an average primary particle diameter of more than 100 nm were used, the tear strength was low and the acoustic wave sensitivity was unacceptable in both cases. In Comparative Example 7, the average primary particle diameter was within the range of the present invention; however, since silica particles that had not been subjected to a surface treatment were used, the viscosity of the composition for an acoustic wave probe before curing was high, and the composition could not be kneaded.

In contrast, it can be seen from Examples 1 to 20 that the compositions of the present invention have predetermined viscosity, and as the compositions are cured, silicone resins each having an acoustic impedance close to the acoustic impedance of a living body, having the acoustic attenuation suppressed, and having excellent tear strength as well as excellent abrasion resistance are obtained.

From the results, it can be seen that the composition for an acoustic wave probe of the present invention is useful for a medical member. In addition, it can be seen that the silicone resin for an acoustic wave probe of the present invention can also be suitably used in at least one of the acoustic lens and the acoustic matching layer of the acoustic wave probe, the acoustic wave measurement apparatus, and the ultrasound diagnostic apparatus. Particularly, the composition for an acoustic wave probe and the silicone resin for an acoustic wave probe can be favorably used in the ultrasound probe in which cMUT is used as an ultrasonic diagnostic transducer array, the photoacoustic wave measurement apparatus, and the ultrasound endoscope for the purpose of improving the sensitivity.

Having described our invention as related to the present embodiments, it is our intention that the invention not be limited by any of the details of the description, unless otherwise specified, but rather be construed broadly within its spirit and scope as set out in the accompanying claims.

REFERENCE SIGNS LIST

1: acoustic lens
2: acoustic matching layer
3: piezoelectric element layer
4: backing material
7: housing
9: cord
10: ultrasound probe

The invention claimed is:

1. A composition for an acoustic wave probe, comprising the following ingredients (A) to (D):
  (A) a linear polysiloxane having a vinyl group;
  (B) a linear polysiloxane having two or more Si—H groups in a molecular chain;
  (C) a polysiloxane resin; and
  (D) surface-treated silica particles having an average primary particle diameter ranging from 50 nm to less than 100 nm,
  wherein the ingredient (D) has a truly spherical shape.

2. The composition for an acoustic wave probe according to claim 1,
  wherein, in 100 parts by mass of a total of each content of the ingredients (A) to (D), the content of the ingredient (D) is 25 to 70 parts by mass.

3. The composition for an acoustic wave probe according to claim 1,
  wherein, in 100 parts by mass in the total of each content of the ingredients (A) to (D), the content of the ingredient (A) is 20 to 80 parts by mass, the content of the ingredient (B) is 0.1 to 20 parts by mass, and the content of the ingredient (C) is 0.1 to 50 parts by mass.

4. The composition for an acoustic wave probe according to claim 1,
  wherein the ingredient (D) are silica particles subjected to surface treatment using a silane compound.

5. The composition for an acoustic wave probe according to claim 4,
  wherein the ingredient (D) are silica particles subjected to surface treatment using a trimethylsilylating agent.

6. The composition for an acoustic wave probe according to claim 1,
  wherein a methanol hydrophobicity of the ingredient (D) is 40 to 80 mass %.

7. The composition for an acoustic wave probe according to claim 1,
wherein the ingredient (A) has a phenyl group.
8. The composition for an acoustic wave probe according to claim 1,
wherein a mass average molecular weight of the ingredient (A) is 20,000 to 200,000.
9. The composition for an acoustic wave probe according to claim 8,
wherein the mass average molecular weight is 40,000 to 150,000.
10. The composition for an acoustic wave probe according to claim 1,
wherein the ingredient (C) is a polysiloxane resin contains a $R_3SiO_{1/2}$ unit and a $SiO_{4/2}$ unit and has at least two vinyl groups in one molecule,
wherein a molar ratio of the $R_3SiO_{1/2}$ unit to the $SiO_{4/2}$ unit is 0.6 to 1.2, and
wherein R represents a monovalent hydrocarbon group.
11. The composition for an acoustic wave probe according to claim 10,
wherein the ingredient (C) is constituted by the $R_3SiO_{1/2}$ unit and the $SiO_{4/2}$ unit.
12. The composition for an acoustic wave probe according to claim 1, comprising:
0.00001 to 0.01 parts by mass of platinum or a platinum compound with respect to 100 parts by mass of the total of each content of the ingredients (A) to (D).

13. A silicone resin for an acoustic wave probe which is obtained by curing the composition for an acoustic wave probe according to claim 1.
14. An acoustic wave probe, comprising at least one of an acoustic lens containing the silicone resin for an acoustic wave probe according to claim 13 and an acoustic matching layer containing the silicone resin for an acoustic wave probe according to claim 13.
15. An ultrasound probe, comprising:
a capacitive micromachined ultrasonic transducer as an ultrasonic transducer array; and
an acoustic lens containing the silicone resin for an acoustic wave probe according to claim 13.
16. An acoustic wave measurement apparatus, comprising:
the acoustic wave probe according to claim 14.
17. An ultrasound diagnostic apparatus, comprising:
the acoustic wave probe according to claim 14.
18. A photoacoustic wave measurement apparatus, comprising:
an acoustic lens containing the silicone resin for an acoustic wave probe according to claim 13.
19. An ultrasound endoscope, comprising:
an acoustic lens containing the silicone resin for an acoustic wave probe according to claim 13.

* * * * *